United States Patent [19]

Maryanoff et al.

[11] Patent Number: 5,449,677
[45] Date of Patent: Sep. 12, 1995

[54] CYCLIC BENZYLAMINO, BENZYLAMIDO AND BENZYLIMIDO ANTIPSYCHOTIC AGENTS

[75] Inventors: Cynthia A. Maryanoff, New Hope; Allen B. Reitz; Malcolm K. Scott, both of Lansdale, all of Pa.

[73] Assignee: McNeilab, Inc., Spring House, Pa.

[21] Appl. No.: 120,015

[22] Filed: Sep. 10, 1993

Related U.S. Application Data

[63] Continuation-in-part of Ser. No. 943,846, Sep. 11, 1992, Pat. No. 5,314,885.

[51] Int. Cl.⁶ .................. A61K 31/495; A61K 31/445; C07D 403/00; C07D 211/08
[52] U.S. Cl. ...................... 514/253; 514/252; 514/316; 544/372; 544/373; 546/191
[58] Field of Search ................ 544/372, 373; 514/252, 514/253

[56] References Cited

U.S. PATENT DOCUMENTS 5,087,627 2/1992 Morita et al. .............. 544/360
5,177,078 1/1993 Ward et al. ................ 544/360
5,254,689 10/1993 Butera et al. .............. 544/360

Primary Examiner—Cecilia Tsang

[57] ABSTRACT

Compounds of the general formula I

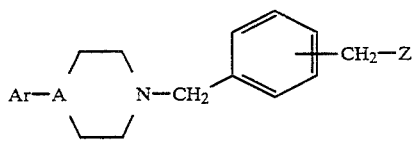

are disclosed as novel antipsychotic agents. Pharmaceutical compositions and methods of treating convulsions employing such compounds of formula I are also disclosed.

13 Claims, No Drawings

CYCLIC BENZYLAMINO, BENZYLAMIDO AND BENZYLIMIDO ANTIPSYCHOTIC AGENTS

This is a continuation-in-part of Ser. No. 943,846, filed Sep. 11, 1992, now U.S. Pat. No. 5,314,885.

BACKGROUND OF THE INVENTION

Antipsychotic drugs are known to alleviate the symptoms of mental illnesses such as schizophrenia. Examples of such drugs include phenothiazine derivatives such as promazine, chlorpromazine, fluphenazine, thioridazine and promethazine, thioxanthenes such as chlorprothixene, butyrophenones such as haloperidol and clozapine. While these agents may be effective in treating schizophrenia, virtually all except clozapine produce extrapyramidal side effects, such as facial tics or tardive dyskinesia. Since antipsychotics may be administered for years or decades to a patient, such pronounced side effects may complicate recovery and further isolate the individual from society.

The present invention describes novel compounds that combine antipsychotic effects with minimal or reduced side effects such as extrapyramidal symptomology relative to some of the compounds known in the art.

SUMMARY OF THE INVENTION

Compounds of the general formula I:

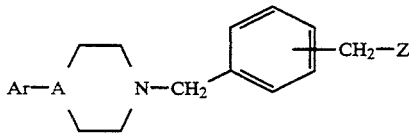

I wherein Ar, A and Z are as defined hereinafter, are potent antipsychotic agents useful in the treatment of psychotic conditions such as schizophrenia in mammals including humans. The compounds of the present invention may also be useful in the treatment of other disorders of the central nervous system such as anxiety and aggression. The present invention is also directed to pharmaceutical compositions containing the compounds of formula I and methods of treating psychotic conditions employing such compounds.

DETAILED DESCRIPTION OF THE INVENTION

The present invention is directed to compounds of the general formula I:

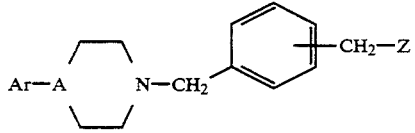

I wherein
A is N or CH, but preferably N.
Ar is aryl or substituted aryl. The aryl group may be independently substituted with one or more of $C_1$–$C_8$ alkyl, $C_3$–$C_{10}$ cycloalkyl, $C_1$–$C_8$ hydroxyalkyl, $C_1$–$C_8$ alkoxy, aryloxy, hydroxyl, trifluoromethyl, trifluoromethoxy, cyano, $C_1$–$C_8$ alkylthio, halogen, nitro, $C_1$–$C_8$ haloalkyl, amino or $C_1$–$C_8$ mono- or dialkylamino. More preferably, Ar is substituted phenyl. The more preferred substituents are selected from any of $C_1$–$C_8$ alkoxy. Most preferably, the substituents is isopropoxy. The preferred site of substitution is the 2-position on the phenyl ring.

Z is a 5- or 6-membered saturated, substituted or unsubstituted ring containing 1 ring nitrogen atom with the remaining ring atoms being carbon. The ring nitrogen is the point of attachment of the 5-or 6-membered ring to the remainder of the molecule. The 5 or 6 membered ring contains 0, 1 or 2 carbonyls adjacent the ring N. Optionally, the 5- or 6-membered ring may be attached to a four membered carbon moiety to form a 6-membered fused aromatic ring or may be attached to a four membered carbon moiety to form a 5-membered spirocycle. The substituents on the 5- or 6-membered ring are selected from any of $C_1$–$C_4$ alkyl.

As used herein, unless otherwise noted alkyl and alkoxy whether used alone or as part of a substituent group, include straight and branched chains. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl, 2-methylpentyl. Alkoxy radicals are oxygen ethers formed from the previously described straight or branched chain alkyl groups. Of course, if the alkyl or alkoxy substituent is branched there must be at least 3 carbon atoms.

The term "aryl" as used herein alone or in combination with other terms indicates aromatic hydrocarbon groups such as phenyl or naphthyl. With reference to substituents, the term independently means that when more than one of such substituent is possible such substituents may be the same or different from each other.

There is a 1,2-, 1,3-, or 1,4-relationship of the $CH_2Z$ and $CH_2$-piperidine or $CH_2$-piperazine substituents on the appropriate aromatic ring.

Examples of particularly preferred compounds include:

1-[[3-[[1-[2-(1-Methylethoxy)phenyl]-4-piperazinyl]methyl]phenyl]methyl]-piperidin-2-one;
1-[[4-[[1-[2-(1-Methylethoxy)phenyl]-4-piperazinyl]methyl]phenyl]methyl]-piperidin-2-one;
1-[[2-[[1-[2-(1-Methylethoxy)phenyl]-4-piperazinyl]methyl]phenyl]methyl]piperidin-2-one;
1-[[3-[[1-[2-(1-Methylethoxy)phenyl]-4-piperazinyl]methyl]phenyl]methylpiperidine-2,6-dione;
2-[[3-[[1-[2-(1-Methylethoxy)phenyl]-4-piperazinyl]methyl]phenyl]methyl -1H-isoindole-1,3 (2H)-dione;
1-[[3-[[1-[2-(1-Methylethoxy)phenyl]-4-piperazinyl]methyl]phenyl]methyl]pyrrolidine-2,5-dione;
8-[[3-[[1-[2-(1-Methylethoxy)phenyl]-4-piperazinyl]methyl]phenyl]methyl]-8-azaspiro[4.5]decane-7,9-dione;
1-Methyl-1-[[3-[[1-[2-(1-methylethoxy)phenyl]-4-piperazinyl]methyl]phenyl]methyl]-piperidine-2,6-dione; and
1-[[4-[[1-[2-(1-Methylethoxy)phenyl]-1 -piperazinyl]methyl]phenyl]methyl]pyrrolidine.
1-[[3-[[1-[2-(1-Methylethoxy)phenyl]-4-piperidinyl]methyl]phenyl]methyl]-piperidin-2-one Within the scope of the invention are compounds of the invention in the form of hydrates and other solvate forms.

Representative salts of the compounds of formula I which may be used include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicyclic, p-aminosalicyclic, 2-phenoxybenzoic, 2-acetoxybenzoic or a salt made with saccharin. Such salts can be made by reacting the free base of formula I with the acid and recovering the salt.

The compounds of formula I may be prepared according to the following reaction schemes.

32, 1051). The cyanobenzyl bromide is also commercially available from Aldrich Chemical Co.

REACTION SCHEME 2

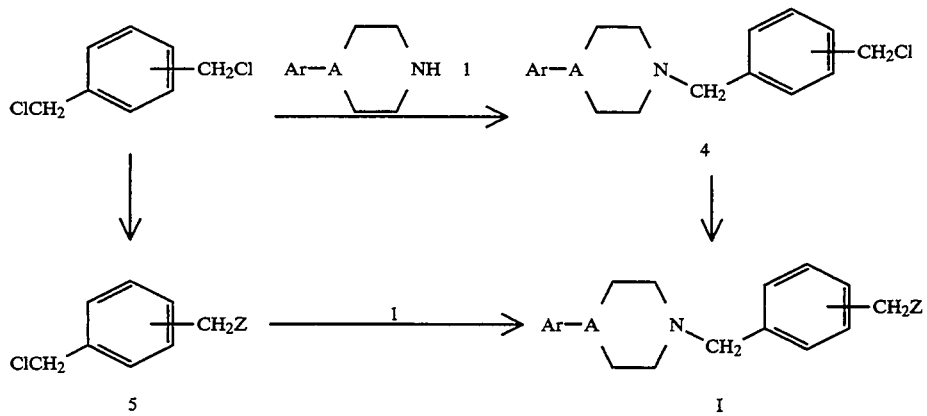

In Reaction Scheme 2, compounds of formula I are prepared by treating a compound of formula 4 with (i) a metal salt of a suitable lactam, or cyclic imide in DMF or THF, the metal being chosen from sodium, lithium, or potassium and the like or (ii) a suitable cyclic amine. This route utilizing compound 4 is useful in making compounds wherein there is a 1,3- or 1,4- substitution on the phenyl ring. Alternatively, compounds of formula 1 may be obtained by the reaction of compounds

REACTION SCHEME 1

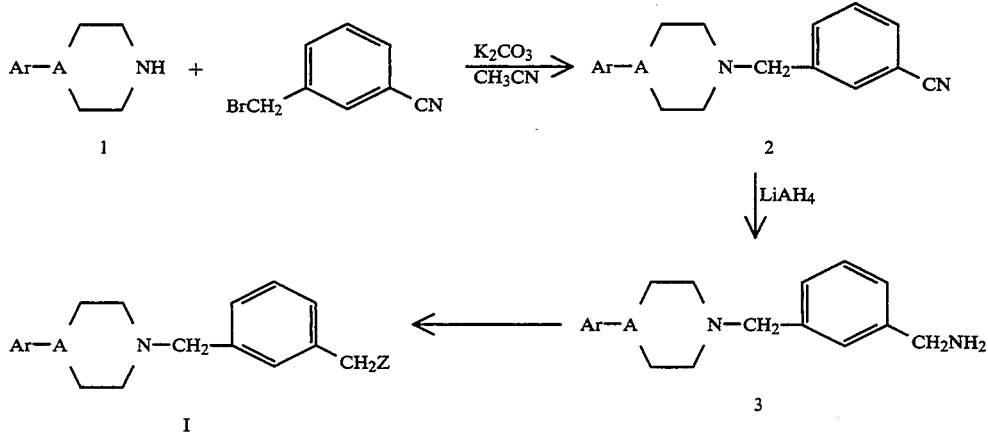

In Reaction Scheme 1, the aryl piperazine or piperidines of formula I are reacted with 3-cyanobenzyl bromide in the presence of a base such as $K_2CO_3$ and a suitable solvent such as $CH_3CN$ to produce compound 2. Compound 2 is then reduced in the presence of a suitable reducing agent such as $LiAlH_4$ in a suitable solvent such as ether or THF to produce amine 3.

Compounds of formula I are prepared by treating compounds of formula 3 with the appropriate cyclic anhydride in toluene to give imides, or with thionyl chloride in THF to afford sulfonamides, or in the presence of acetic anhydride or an acyl chloride in THF, methylene chloride, or chloroform to provide amides.

The aryl piperazines and piperidines (i.e. 1) are commercially available from Aldrich Chemical Co. or may be prepared by standard methods known in the art (for example, see G. E. Martin et al., J. Med. Chem., 1989, of formula 5 with compounds of formula I in a suitable solvent such as DMF in the presence of a base such as triethylamine. Compounds of formula 4 are obtained by the reaction of suitable α,α'-di(chloromethyl)-benzenes with compounds of formula 1 in a suitable solvent such as DMF or THF in the presence of bases such as diisopropylethyl amine. Compounds of formula 5 are prepared by treating a suitable α,α'-di(chloromethyl)benzene with a metal salt of a suitable lactam or cyclic imide in a suitable solvent such as THF, the metal being chosen from sodium, lithium, or potassium and the like. This route going through compound 5 is useful in making compounds wherein there is 1,2-, 1,3- or 1,4-substitution on the phenyl ring. The lactams, imides, cyclic imides, and cyclic amines are commercially available.

The antipsychotic activity of the compounds of the invention may be determined by the Block of Conditioned Avoidance Responding (Rat) test (CAR), references being Cook, L. and E. Weidley in *Ann. N.Y. Acad. Scio.*, 1957, 6, 740–752, and Davidson, A. B. and E. Weidley in *Life Sci.*, 1976, 18, 1279–1284. This test was performed for compounds disclosed in this invention, and the data are listed in Table 1.

Block of Conditioned Avoidance Responding (Rat)

Apparatus: Rat operant chambers, housed within sound attenuated booths, both from Capden Instruments Ltd., were used in this test. The test chamber (8"H×9⅜" W×9" D) is constructed of aluminum and plexiglass with floor grid bars of stainless-steel (⅛" O.D.) spaced 9/16" apart. A stainless-steel operation level 1½" wide projects ¾" into the chamber and is positioned 22/8" above the grid floor. The shock stimulus is delivered via the grid floor by a Coulbourn Instruments solid state module. The parameters of the test and the collection of data are controlled automatically.

Training: Male, Fischer 344 rats obtained from Charles River (Kingston, N.Y.) weighing more than 200 g, are individually housed with chow and water provided ad libitum. The rats are trained for two weeks to approach criterion levels in the avoidance test (90% avoidance rate). One-hour training sessions are run at about the same time each day for four or five days a week. The training session consists of 120 trials, with the conditioned stimuli presented every 30 sec. A trial begins with presentation of the conditioned stimuli (a light and a tone). If the rat responds by depressing the operant lever during the 15-second presentation of the conditioned stimuli, the trial is terminated and the animal is credited with a CAR. Failure to respond during the conditioned stimuli causes the presentation of the unconditioned stimulus (UCS), a 0.7 mA shock which is accompanied by a light and tone for five seconds. If the rat depressed the lever within the ten-second period, the shock and trial are terminated and an escape response recorded. If the rat fails to depress the lever during the UCS (shock), the trial is terminated after ten seconds of shock and the absence of a response is scored as a failure to escape. Intertial level presses have no effect. If a rat performs at the 90% CAR level for two weeks, it is then run twice a week on the test schedule (see below) until baseline performance stabilized. Before any drug is administered, two weeks of CAR at a rate of 90% or better is required.

Determination of ED$_{50}$ Values

Trained rats are run in a one-hour session on two consecutive days at the same time and in the same test chamber each day. The sessions consist of 60 trials, one every minute. The conditioned stimuli are presented for 15 sec (maximum) and the unconditioned stimuli five sec (maximum). On Day 1, a vehicle solution is administered to the rats at a time preceding the trial run corresponding to the pretreatment time for the test compound. The route of administration and the volume of vehicle are also matched to that of the test compound. Only animals that exhibited greater than 90% CAR on Day 1 are given the test compound on Day 2.

Statistical Computations: ED$_{50}$ values (that dose required to reduce the mean number of CARS to 50% of the control mean) are determined in the following manner. The percent change in CAR on the drug treatment day compared to vehicle pretreatment day is the key measure. The percent change (% change) in CAR is determined using the following formula:

% change CAR=((Day 2% CAR/Day 1% CAR)×100)−100

A negative number indicates a blockade of CAR, whereas a positive number would indicate increased CAR. The test results are reported as the mean % change for the group of rats. A reading of −20% is generally taken to represent a minimum value for a compound to be designated as active at a given dose in the CAR test. Failure to escape was calculated for each animal as follows:

% Failures=#of Failures to Escape/#of trials

The % failures, viz., loss of escape, is also reported as a group mean. Failures to escape are monitored closely and a session is terminated if ten failures occurred. ED$_{50}$ values and 95% confidence limits are calculated using linear regression analysis. The results of the CAR tests are shown in Table 1.

Receptor Binding Assay

The dopamine D$_2$ binding activity of compounds was determined using a P$_2$ fraction (synaptosomal membranes) prepared from male, Wistar rats. The D$_2$ assay employed a P$_2$ fraction from the striatum, the ligand $^3$H-spiperone at a concentration of 0.05 nM, and 1 mM haloperidol as a blank determinant. Incubation was in 3 mM potassium phosphate buffer for 45 min at 37° C. Under these conditions, specific binding constituted 75% of total binding, and the K$_I$ values for some known drugs were: 0.37 nM for haloperidol and 82 nM for clozapine.

The data from this assay were analyzed by calculating the percent inhibition of the binding of the tritiated ligands by given concentrations of the test compound. K$_I$ values, where given, were obtained from the logit analysis of concentration-inhibition curves. A value of 1000 or less is generally taken to represent the value for a compound to be designated as active in this screen. If a compound is active in this screen, but not in the CAR screen, it is still considered an active antipsychotic agent because the CAR screen negative result may be due to site delivery problems which may be solved by a suitable delivery mechanism. The D$_2$ binding results are shown in Table 1. The compound numbers used in Table 1 refer to specific compounds described in the Examples.

TABLE 1

| CP# | % inhibition CAR, 5 mpk, po | % escape loss | Receptor Binding K$_I$ mM) D2 |
|---|---|---|---|
| 1 | −89 | 12 | 117 |
| 2 | −29 | 1 | 23 |
| 3 | −6. | 0 | 46 |
| 4 | −16 | 0 | 63 |
| 5 | −8 | 1 | 57 |
| 6 | −68 | 29 | 94 |
| 7 | 0 | 0 | 20 |
| 8 | −70 | 5.6 | 17 |
| 9 | −68 | 25.4 | 20 |

To prepare the pharmaceutical compositions of this invention, one or more compounds or salts thereof of the invention, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 50 to about 100 mg of the active ingredient, although other unit dosages may be employed.

In therapeutic use as an antipsychotic agent, the compounds of this invention may be administered in an amount of from about 0.5 to 5 mg/kg per day, and more preferably 1–3 mg/kg per day. The dosages, however may be varied depending upon the requirements of the patient, the severity of the condition being treated, and the compound being employed. Determination of optimum dosages for a particular situation is within the skill of the art.

The following examples describe the invention in greater detail and are intended to illustrate the invention, but not to limit it. In the Examples, the CP # refers to the CP # in Table 1 and not to the numbers employed in the Reaction Scheme. In the Examples, the terms $^1$H NMR, mass spectral analysis FAB-MS and IR indicate that the compounds produced were analyzed using such analyses and the results confirmed the structure.

EXAMPLE 1

1-[[3-[[1-[2-(1-Methylethoxy)phenyl]-4-piperazinyl]methyl]phenyl]methyl]piperidin-2-one     Hydrochloride (3:2) (CP #1)

A solution of N-[2-(1-methylethoxy)phenyl]piperazine (11.95 g, 54.3 mmol, prepared as described by Martin and Scott, et. al. *J. Med. Chem.*, 1989, 32, 1052–1056), in THF (250 mL) was treated with α,α'-dichloro-m-xylene (23.7 mL, 0.163 mol) and refluxed. After 4 h, diisopropylethylamine (10.4 mL, 55 mmol) was added and the solution was refluxed an additional 1.5 h. Treatment with 1N HCl (120 mL), water (50 mL), and ether (200 mL) caused a white solid to form which was collected by filtration. This material (7.40 g, 18.73 mmol) was partitioned into saturated aqueous NaHCO$_3$ to give 6.0 g of an oil. A solution of this material in THF (10 mL) was added to a solution of gamma-valerolactam (1.74 g, 17.5 mmol) in THF (80 mL) which had been treated at 0° C. with 2.5M n-BuLi/hexane (7.0 mL, 1 mol-eqiv). The resulting solution was heated at reflux for 1.5 h, treated with a suspension of gammavalerolactam (500 mg, 5.05 mmol) and 2.5M n-BuLi/hexane (2.0 mL) in THF (10 mL) and refluxed an additional hour. The solution was cooled and partitioned between water and ether. The ether layer was separated, dried, filtered, and concentrated to give a yellow oil. This material was purified on two Waters Prep-500 silica gel columns (EtOAc/hexane; 8:2), affording 1-[[3-[[1-[2-(1-methylethoxy)phenyl]-4-piperazinyl]methyl]phenyl]-methylpiperidin-2-one as an oil, 4.80 g. A solution of this oil in i-PrOH (30 mL) was treated with conc HCl (1.15 mL) followed by ether (ca. 500 mL). A white solid was collected by filtration and recrystallized from i-PrOH/ether affording 1-[[3-[[1-[2-(1-methylethoxy)-phenyl]-4-piperazinyl]methyl]phenyl]methyl]-piperidin-2-one hydrochloride (3:2) as a white crystalline solid (3.74 g, 44%), m.p. 206°–208° C. Both $^1$H-NMR and FAB-MS supported the assigned structure.

Elemental Analysis: Calculated for $C_{26}H_{35}N_3O_2 \cdot 1.5$ HCl: C, 65.57; H, 7.72 N, 8.82; Cl, 11.17. Found: C, 65.29; H, 7.78; N, 8.68; Cl, 10.95.

EXAMPLE 2

1-[[4-[[1-[2-(1-Methylethoxy)phenyl]-4-piperazinyl]methyl]phenyl]methyl]-piperidin-2-one     Hydrochloride (5:1) (CP #2)

Prepared as in Example 1, using α,α'-dichloro-p-xylene in place of α,α'-dichloro-m-xylene, was 1-[[4-[[1-[2-(1-methylethoxy)phenyl]-4-piperazinyl]methyl]-phenyl]methyl]-piperidin-2-one hydrochloride (5:1; 2.45 g, 30%), m.p. 196°–206° C.

Elemental Analysis: Calculated for $C_{26}H_{35}N_3O_2 \cdot 0.2$ HCl: C, 63.15; H, 7.54; N, 8.49. Found: C, 63.60; H, 7.44; N, 8.51

EXAMPLE 3

1-[[2-[[1-[2-(1-Methylethoxy)phenyl]-4-piperazinyl]methyl]phenyl]methyl]-piperidin-2-one     Hydrochloride (3:2) (CP #3)

A solution of γ-valerolactam (7 g, 70.5 mmol) in THF (150 mL) and DMSO (20 mL) was treated with NaH (2.83 g of a 60% oil dispersion) at 0° C. under nitrogen atmosphere. After a total of 15 min, α,α(-dichloro-o-xylene (25 g, 140 mmol) was added and the solution was allowed to warm and stir at room temperature. After 4 h, 100 mL of ether and 100 mL of 0.2N HCl were added. The water was withdrawn, and the organic layer was washed 2× more with water, dried (MgSO$_4$), filtered and concentrated. This material was purified on ca. 400 g of silica gel (flash chromatography; EtOAc/hexane 7:3) to yield N-[2-(chloromethyl)benzyl]-γ-valerolactam (6.6 g, 40%). 1H NMR and mass spectral analysis supported the assigned structure. A solution of this lactam (5.0 g, 21.09 mmol), 2-(isopropoxy)phenyl-piperazine fumarate (6.38 g, 18.99 mmol), and triethylamine (8.82 mL, 62.37 mmol)in DMF (75 mL) was heated for 3 h at 50°–60° C. After 3 h, the solution was added to a 3:1 solution of ether/ethyl acetate (ca. 100 mL) and extracted 3× with water, dried (MgSO$_4$), filtered and concentrated. The residual oil was purified on ca. 400 g of silica gel (flash chromatography, EtOAc/hexane, 6:4) to give 5.41 g of white semi-solid, pure by thin layer chromatography. It was then dissolved in iPrOH, filtered through a Millipore filter, treated with 2.44 mL of conc. aqueous HCl (ca. 26 mmol), and then triturated out of solution by the addition of ether. The resultant white solid was recrystallized in MeOH/ether to give 1-[[2-[[1-[2-(1-methylethoxy)phenyl]-4-piperazinyl]methyl]phenyl]methyl]-piperidin-2-one hydrochloride (3:2) as a white powder (5.50 g, 61%), m.p. 249.5°–252.5° C. $^1$H NMR and mass spectral analysis supported the assigned structure.

Elemental Analysis Calculated for $C_{26}H_{35}N_3O_2 \cdot 1.5HCl \cdot 0.3H_2O$; C, 64.83; H, 7.76; N, 8.72; Cl, 11.04; $H_2O$, 1.12. Found: C, 64.90; H, 7.69; N, 8.70; Cl, 13.40; $H_2O$, 0.96.

EXAMPLE 4

1-[[3-[[1-[2-(1-Methylethoxy)phenyl]-4-piperazinyl]methyl]phenyl]methyl]-piperidine-2.6-dione (Z)-2-Butenedioate (1:1) (CP #4)

A mixture of NaH (0.224g, 7.48 mmol) and DMF (10 mL) was treated slowly with 2,6-piperidinedione (0.846 g, 7.48 mmol) at room temperature. After the addition was complete, the mixture was cooled to 0° C. and a solution of 3-[3-[[1-[2-(1-methylethoxy)phenyl]-4-piperazinyl]methyl]benzyl chloride (2.46 g, 7.12 mmol) and DMF (10 mL) was added dropwise. The cooling bath was removed and the reaction was stirred at room temperature overnight. A small portion of water was added and the reaction was concentrated under vacuum. The residue was partitioned between $CH_2Cl_2$/water and the organic layer was separated, dried, and evaporated to give 1-[[3-[[1-[2-(1-methylethoxy)phenyl]-4-piperazinyl]methyl]phenyl]methyl]-piperidine-2,6-dione as an oil, 3.25 g. This material was dissolved in i-PrOH (13 mL) and treated with maleic acid (0.83 g, 7.15 mmol). Trituration with ether, filtration, and drying afforded 1-[[3-[[1-[2-(1-methylethoxy)phenyl]-4-piperazinyl]methyl]phenyl]methyl]-piperidine-2,6-dione (Z)-2-butenedioate (1:1) as a white solid (2.73 g, 70%), m.p. 103°–105° C. $^1$H NMR and mass spectral analysis supported the assigned structure.

Elemental Analysis Calculated for $C_{26}H_{33}N_3O_2 \cdot C_4H_4O_4$: C, 65,32; H, 6.76; N, 7.62. Found: C, 65.32; H, 6.94; N, 7.62.

EXAMPLE 5

2-[[3-[[1-[2-(1-Methylethoxy)phenyl]-4-piperazinyl]methyl]phenyl]methyl]-1H-isoindole-1,3 (2H)-dione Z)-2-Butenedioate (1:1) (CP #5)

Prepared as described in Example 4, using phthalimide in place of 2,6-piperidinedione, was 2-[[3-[[1-[2-(1-methylethoxy)phenyl]-4-piperazinyl]methyl]phenyl]methyl]-1H-isoindole-1,3(2H)-dione (Z)-2-butenedioate (1:1; 3.89 g, 88%), m.p. 143°–145° C. $^1$H NMR and mass spectral analysis supported the assigned structure.

Elemental Analysis Calculated for $C_{29}H_{31}N_3O_3 \cdot C_4H_4O_4$: C, 67.68; H, 6.02; N, 7.17. Found: C, 67.71; H, 5.93; N, 7.16.

EXAMPLE 6

1-[[3-[[1-[2-(1-Methylethoxy)phenyl]-4-piperazinyl]methyl]phenyl]methyl]pyrrolidine-2,5-dione (Z)-2-Butenedioate (1:1) (CP #6)

Prepared as described in Example 4, using succinimide in place of 2,6-piperidinedione, was 2-[[3-[[1-[2-(1-methylethoxy)phenyl]-4-piperazinyl]methyl]phenyl]methyl]pyrrolidine-2,5-dione (Z)-2-butenedioate (1:1; 3.54 g, 87%), m.p. 105°–108° C. $^1$H NMR and mass spectral analysis supported the assigned structure.

Elemental Analysis Calculated for $C_{25}H_{31}N_3O_3 \cdot C_4H_4O_4$: C, 64.79; H, 6.56; N, 7.82. Found: C, 64.57; H, 6.48; N, 7.82.

EXAMPLE 7

8-[[3-[[1-[2-(1-Methylethoxy)phenyl]-4-piperazinyl]methyl]phenyl]methyl]-8-azaspiro[4.5]decane-7,9-dione Dihydrochloride (CP #7)

A solution of 3-cyanobenzyl bromide (10.0 g, 0.051 mol), commercially available from Aldrich Chemical, and acetonitrile (250 mL) was added to a mixture of N-[2-(methylethoxy)phenyl]piperazine hydrochloride (13.10 g, 0.051 mol, prepared according to Martin, G. E., et al, *J. Med. Chem.*, 1989, 32, 1052), $K_2CO_3$ (21.15 g, 0.153 mol) and acetonitrile (250 mL) and the resulting mixture was stirred at reflux under nitrogen for 6.75 hours. The reaction was cooled, concentrated to dryness, and the residue partitioned between $CH_2Cl_2$ and aqueous $NaHCO_3$. The organic layer was separated, dried over anhydrous $Na_2SO_4$, and evaporated to give a gummy residue. This material was chromatographed on silica gel ($CH_3OH:CH_2Cl_2/2:98$ eluant) to produce 3-[[1-[2-(1-methylethoxy)phenyl]-4-piperazinyl]methyl]benzonitrile as a yellow gum, 10.86 g. A solution of this material (10.36 g, 0.031 mol) and anhydrous ether (500 mL) was added dropwise to a slurry of $LiAlH_4$ (1.17 g, 0.031 mol) in anhydrous ether (500 mL) under $N_2$ at room temperature. The reaction was stirred at reflux for 5.5 hours at which point additional $LiAlH_4$ (1.17 g, 0.031 mol) was added. After stirring at reflux for 12 hours, the reaction was cooled in an ice bath and treated slowly with $H_2O$ (100 mL), 20% aqueous NaOH (100 mL), and $H_2O$ (100 mL) in that order, followed by extraction with diethyl ether. The ether layer was separated, dried over anhydrous $Na_2SO_4$, filtered, and evaporated to give 3-[[1-[2-(1-methylethoxy)phenyl]-4-piperazinyl]methyl]benzyl amine as a pale yellow gum, 8.07 g.

A solution of 3-[[1-[2-(1-methylethoxy)phenyl]-4-piperazinyl]methyl]-benzyl amine (2.50 g, 7.37 mmol), prepared as described above, 3,3-tetramethyleneglutaric anhydride (1.12 g, 6.66 mmol), and toluene (30 mL) was heated to reflux, cooled slightly, and treated with thionyl chloride (9.72 mL, 13.32 mmol). The resulting slurry was refluxed for 30 min, cooled and the solid collected by filtration. This material was partitioned between $CH_2Cl_2$/3N NaOH and the organic layer was separated, dried, filtered and evaporated giving 8-[[3-[[1-[2-(1-methylethoxy)phenyl]-4-piperazinyl]methyl]phenyl]methyl]-8-azaspiro[4.5]decane-7,9-dione as a crude oil. The oil was converted to the maleate salt in i-PrOH. The isolated residue was converted back to the free base which was obtained as an oil (2.10 g). Chromatography of this material on flash silica using EtOAc/hexane of varying proportions gave an oil which was dissolved in ether and added to ethereal HCl causing formation of a solid. Filtration afforded 8-[[3-[[1-[2-(1-methylethoxy)phenyl]-4-piperazinyl]methyl]phenyl]methyl]-8-azaspiro[4.5]decane-7,9-dione dihydrochloride (0.94 g, 25%), m.p. 212°–216° C. (dec). $^1$H NMR and mass spectral analysis supported the assigned structure.

Elemental Analysis Calculated for $C_{30}H_{39}N_3O_3 \cdot 2.0$ HCl: C, 64.05; H, 7.35; N, 7.47; Cl, 12.60. Found: C, 63.90; H, 7.32; N, 7.40; Cl, 12.72.

EXAMPLE 8

1-Methyl-1-[[3-[[1-[2-(1-methylethoxy)phenyl]-4-piperazinyl]methyl]phenyl]methyl]-piperidine-2,6-dione Dihydrochloride (CP #8)

A solution of 3-[[1-[2-(1-methylethoxy)phenyl]-4-piperazinyl]methyl]benzyl amine (2.32 g, 6.84 mmol; prepared as described in Example 7), 3-methylglutaric anhydride (0.88 g, 6.84 mmol), and THF (20 mL) was stirred at room temperature for 3 h and then concentrated to an oily residue. This material was dissolved in acetic anhydride (25 mL), heated at 100° C. for 4 h, cooled, and added slowly to saturated aqueous NaHCO$_3$. Extraction with CH$_2$Cl$_2$, separation of the organic layer, drying, filtration and evaporation afforded an oil. This material was chromatographed on flash grade silica using 97:3/CH$_2$Cl$_2$:MeOH to give 4-methyl-1-[[3-[[1-[2-(1-methylethoxy)phenyl]-4-piperazinyl]methyl]-phenyl]methyl]piperidine-2,6-dione as an oil. This was dissolved in ether and added to ethereal HCl causing a solid to form. Filtration afforded 4-methyl-1-[[3-[[1-[2-(1-methylethoxy)phenyl]-4-piperazinyl]methyl]-phenyl]methyl]piperidine-2,6-dione dihydrochloride (1.43 g, 40%), m.p. 196°–200° C. H-1 NMR and mass spectral analysis supported the assigned structure.

Elemental Analysis Calculated for C$_{27}$H$_{35}$N$_3$O$_3$.2.0 HCl.0.25 H$_2$O: C, 61.53; H, 7.17; N, 7.97; H$_2$O, 0.90. Found: C, 61.57; H, 7.27; N, 7.89; H$_2$O, 1.90.

EXAMPLE 9

1-[[4-[[1-[2-(1-Methylethoxy)phenyl]-4-piperazinyl]methyl]phenyl]methyl]pyrrolidine Dihydrochloride hydrate (4:3) (CP #9)

A solution of α,α'-dichoro-p-xylene(30.40 g ,0.174 mol), N-[2-(1-methylethoxy)phenyl]piperazine (12.70 g, 0.058 mol), triethylamine (6.08 g, 0.06 mol), and THF (200 mL) was refluxed for 4 h. Ether (100 mL) and 1N HCl (100 mL) were added producing a white suspension which was filtered to give 4-[[1-[2-(1-methylethoxy)phenyl]-4-piperazinyl]methyl]benzyl chloride hydrochloride.

A solution of 4-[[1-[2-(1-methylethoxy)phenyl]-4-piperazinyl]methyl]benzyl chloride hydrochloride (5.0 g, 0.012 mol), pyrrolidine (8.95 g, 0.126 mol), excess triethylamine, and THF (50 mL) was stirred at room temperature for 24 h. The reaction was then diluted with methylene chloride and washed with water. The organic layer was separated, dried (Na$_2$SO$_4$), filtered, and evaporated to a yellow oil. The residue was chromatographed on silica gel using 95:4.5:0.5/CHCl$_3$:MeOH:NH$_4$OH as eluant to give 1-[[4-[[1-[2-(1-methylethoxy)phenyl]-4-piperazinyl]methyl]phenyl]methyl]pyrrolidine as an oil, 5.00 g (100%). This material (4.95 g, 0.013 mol) was dissolved in i-PrOH (100 mL) and acidified with concentrated HCl to pH 3. The resulting solid was collected by filtration to give 1-[[4-[[1-[2-(1-methylethoxy)phenyl]-4-piperazinyl]methyl]phenyl]methyl]pyrrolidine dihydrochloride hydrate as a white powder, 4.83 g (80%), m.p. 270–280 (browning) 280°–300° C. $^1$H NMR and mass spectral analysis supported the assigned structure.

Elemental Analysis Calculated for C$_{25}$H$_{35}$N$_3$O.2 HCl.0.75 H$_2$O: C, 62.55; H, 7.87; N, 8.75; Cl, 14.77; H$_2$O, 2.81. Found: C, 62.47; H, 7.19; N, 8.75; Cl, 14.93; H$_2$O, 1.21.

EXAMPLE 10

1-[[3-[[1-2-(1-Methylethoxy)phenyl]-4-piperidinyl]methyl]phenyl]methyl]-piperidin-2-one (CP #10)

A biphasic solution of α,α'-dichloro-m-xylene (2.40 g, 0.0137 mol), N-[2-(1-methylethoxy)phenyl]piperidine (3.00 g, 0.0137 mol), sodium carbonate (2.19 g, 0.020 mol), ethyl acetate (20 mL), and H$_2$O (20 mL) was refluxed for 3 h. The organic layer was separated, dried (MgSO$_4$), filtered, and evaporated to an oil. The residue was chromatographed on silica gel using chloroform as eluant to give 3-[[1-[2-(1-methylethoxy)phenyl]-4-piperidinyl]methyl]benzyl chloride (1.25 g, 25%).

A solution of 3-[[1-[2-(1-methylethoxy)phenyl]-4-piperidinyl]methyl]benzyl chloride (5.25 g, 0.0147 mol) in THF (90 mL) was added dropwise to a solution of γ-valerolactam (2.06 g, 0.02 mol) in THF (50 mL) which had been treated at 0° C. with 1.6M n-BuLi/hexane (12 mL, 1 mol equiv). The resulting solution was heated to reflux for 3 h, cooled, and quenched with MeOH (20 mL). The solution was evaporated to dryness to give a yellow oil. The residue was chromatographed on silica gel using 99:1/CHCl$_3$:MeOH as eluant to give 1-[[3-[[1-[2-(1-methylethoxy)phenyl]-4-piperidinyl]methyl]phenyl]methyl]-piperidin-2-one as a light yellow oil, 1.41 g (23%). MS (Cl CH$_4$): m/e 421 (MH+). $^1$H NMR (CDCl$_3$): δ1.3 (d, 6H), 1.8 (m, 4H), 2.0 (m, 2H), 2.4 (s, 1H), 2.9 (m, 3H), 3.2 (m, 2H), 3.6 (s, 1H), 3.7 (d, 1H), 4.6 (m, 3H), 5.0 (s, 1H), 6.9 (m, 2H), 7.1 (m, 2H), 7.3–7.6 (m, 4H).

We claim:

1. A compound of the formula I:

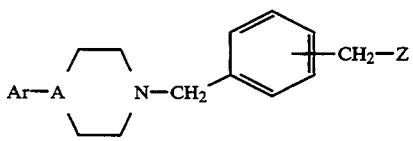

wherein

A is N

Ar is aryl or substituted aryl; wherein the aryl substituents for the aryl group are selected from any of C$_1$–C$_8$ alkyl, C$_3$–C$_{10}$ cycloalkyl C$_1$–C$_8$ hydroxyalkyl, C$_1$–C$_8$ alkoxy, aryloxy, hydroxyl, trifluoromethyl, trifluoromethoxy, cyano, C$_1$–C$_8$ alkylthio, halogen, nitro, C$_1$–C$_8$ haloalkyl, amino or C$_1$–C$_8$ mono- or di- alkylamino;

Z is isoindolyl or pyrrolidinyl, optionally substituted with a C$_1$–C$_4$ alkyl;

there is a 1,2-, 1,3-, or 1,4-relationship of the CH$_2$Z and CH$_2$—piperazine or moieties on the appropriate aromatic ring.

2. The compound of claim 1, wherein Ar is substituted phenyl.

3. The compound of claim 2, wherein the substituent is C$_1$–C$_8$ alkoxy.

4. The compound of claim 3, wherein the substituent is isopropoxy.

5. The compound of claim 4, wherein the substituent is substituted in the 2 position on the phenyl ring.

6. The compound of claim 1, wherein the Z substituent is a single methyl.

7. The compound of claim 1, having the name 2-[[3-[[1-[2-(1-methylethoxy)phenyl]-4-piperazinyl]methyl]-phenyl]methyl]-1H-isoindole-1,3 (2H)-dione.

8. The compound of claim 1, having the name 1-[[3-[[1-[2-(1-methylethoxy)phenyl]-4-piperazinyl]methyl]-phenyl]methyl]-pyrrolidine-2,5dione.

9. The compound of claim 1, having the name 1-[[4-[[1-[2-(1-methylethoxy)phenyl]-4-piperazinyl]methyl]-phenyl]methyl]pyrrolidine.

10. A composition for treating psychotic conditions in mammals comprising the compound of claim 1 and a pharmaceutically acceptable carrier, said compound being present in a therapeutically effective amount for treating psychotic conditions in mammals.

11. A method for treating psychotic conditions in mammals comprising administering to a mammal in need of such treatment the compound of claim 1 in an amount sufficient to treat such conditions.

12. The method of claim 11, wherein the condition is schizophrenia.

13. The method of claim 11, wherein the effective amount is about 0.5 to 5 mg/kg per day.

* * * * *